United States Patent [19]

Ikari et al.

[11] Patent Number: 4,670,288
[45] Date of Patent: Jun. 2, 1987

[54] CHEMICALLY-ACTIVE COMPOSITION CONTAINING DIVALENT IRON IONS

[75] Inventors: Yoshikatsu Ikari; Shoichiro Yokoyama, both of Yatabe; Chiaki Ohama; Ryosuke Fukui, both of Tokyo, all of Japan

[73] Assignees: Director-General of Agency of Industrial Science and Technology; Minato Sangyo Co., Ltd., both of Tokyo, Japan

[21] Appl. No.: 743,710
[22] PCT Filed: Sep. 25, 1984
[86] PCT No.: PCT/JP84/00457
  § 371 Date: May 24, 1985
  § 102(e) Date: May 24, 1985
[87] PCT Pub. No.: WO85/01512
  PCT Pub. Date: Apr. 11, 1985

[30] Foreign Application Priority Data

Sep. 24, 1983 [JP] Japan ............... 58-176624
Mar. 24, 1984 [JP] Japan ............... 59-56490
Mar. 27, 1984 [JP] Japan ............... 59-57408
Jul. 17, 1984 [JP] Japan ............... 59-148363
Sep. 1, 1984 [JP] Japan ............... 59-183511
Sep. 20, 1984 [JP] Japan ............... 59-197043

[51] Int. Cl.$^4$ ............... A01G 5/06; B28B 3/18
[52] U.S. Cl. ............... 427/4; 47/58; 106/15.05; 106/18.11; 106/18.26; 426/335

[58] Field of Search ............... 106/18.26, 18.11, 15.05; 47/58; 427/4; 426/335

[56] References Cited

U.S. PATENT DOCUMENTS 1,797,572  3/1931  Fulton et al. ............... 426/335
2,381,487  8/1945  Cook et al. ............... 106/18.12
4,110,508  8/1978  Isgur et al. ............... 427/180
4,384,972  5/1983  Nakamura et al. ............... 252/188.21

OTHER PUBLICATIONS

Chem. Abst., 55: 889i, Lehman et al, Apr. 11, 1957.

Primary Examiner—Theodore Morris
Attorney, Agent, or Firm—Birch, Stewart, Kolasch & Birch

[57] ABSTRACT

A chemically active composition containing divalent iron ions, wherein an iron (II) compound, ascorbic acid and or citric acid and alum are contained and the ratio between the divalent iron ions in the iron (II) compound and ascorbic acid or citric acid is between 1:0.02 and 0.30 (in the case of ascorbic acid) or 1:0.01 and 0.80 (in the case of citric acid) by weight ratio. The composition is applied in the form of an aqueous solution or solid matter as a deodorant, freshness-preserving agent for foods, growth promoting agent for plants and flame retardant for burnable materials. Not only uni-functional materials can be obtained but also multi-functional materials.

20 Claims, 2 Drawing Figures

CHEMICALLY-ACTIVE COMPOSITION CONTAINING DIVALENT IRON IONS

DESCRIPTION

1. Technical Field

This invention relates to a novel composition containing divalent iron ions having various chemical and physiological effects such as deodorization, bactericidal action, freshness-preservation of foods, promotion of plant growth and flame-proofing (flame-retardation) of burnable materials.

2. Background Art

Iron (II) compounds such as ferrous sulfate have a wide variety of utility. However as is well-known, divalent iron ions have a nature, when they are left in the form of aqueous solution, of readily undergoing oxidation by dissolved oxygen or air to turn yellowish brown and result in precipitation. It has been practiced to incorporate hydroxylamines, tin compounds or the like as reducing agents in order to avoid the oxidation of the ferrous ions in the aqueous solution but, since these substances are highly toxic to the human body, application uses of aqueous solutions containing divalent iron ions has been limited.

The present inventors have proposed a chemically active aqueous solution and solid substance containing a small amount of L-ascorbic acid together with divalent iron ions as a composition in which an aqueous solution containing divalent iron ions is stabilized and provided with vairous functions (PCT/JP83/099: Japanese Patent Laid-Open No. 132937/1984). However, since this composition itself is an aqueous solution, the storage and the handling of the solution has been troublesome and the method of use been restricted to impregnation and dipping using water absorbing material as the carrier in the case of the solid matter.

DISCLOSURE OF THE INVENTION

The first object of this invention is to provide a composition of an aqueous solution containing divalent iron ions and the drying product thereof (powder, granules) which is further stabilized while maintaining activities. The second object of this invention is to provide new application uses of the thus stabilized chemically active composition containing divalent iron ions. The third object of this invention is to provide novel multi-function materials equipped with one or more of functions at the same time by applying the chemically stable and stabilized composition.

According to this invention, a novel composition containing divalent iron ions, capable of satisfying the foregoing objects, are extremely stable and have various chemical and physiological activities such as deodorization, bactericidal action, preservation of freshness of foods, growth promotion of plants and flame-proofing treatment (flame-retardation) for burnable materials.

This composition is characterized in that it contains an iron (II) compound, ascorbic acid and/or citric acid and alum, and contains the divalent iron ions in the iron (II) compound and ascorbic acid or citric acid in 1:0.02–0.30 (in the case of ascorbic acid) or 1:0.01–0.80 (in the case of citric acid) by weight ratio.

As the examples of the iron (II) compound usable in the composition according to this invention, there can be mentioned iron (II) salts of inorganic acids such as ferrous sulfate, ferrous chloride, ferrous nitrate, ferrous bromide and a ferrous iodide, as well as iron (II) salts of organic acids such as ferrous gallate, ferrous malate and ferrous fumarate. However, the iron (II) compound are not restricted only to those exemplified above but any of the compounds may be used so long as it can be dissolved in water to form divalent iron ions.

While L-ascorbic acid and D-isoascorbic acid are used as ascorbic acid, L-ascorbic acid is preferred.

In this invention, ascorbic acid and citric acid may be used singly or in combination. In the case of the combined use, citric acid may be used in a small amount since it acts in an auxiliary manner as a stabilizer to ascorbic acid.

In this composition, the weight ratio of the iron (II) in the iron (II) compound and ascorbic acid is preferably between 1:0.02 and 0.13 (about 0.006–0.04 mol of ascorbic acid per one mol of ferrous salt by molar ratio) and, more preferably, between 0.05 and 0.13 (0.016–0.04 mol of ascorbic acid per one mol of ferrous salt by molar ratio). If ascorbic acid is used in excess of the upper limit in this invention, the composition is pigmented to impair the economical merit and the freshness-preserving and deodorizing effects. Moreover the stability is reduced. On the other hand, if ascorbic acid is used in an amount which is less than the lower limit, the stability of iron (II) is insufficient. Further, in the case of citric acid, the weight ratio of iron (II) in the iron (II) compound is preferably in a range between 1: less than 0.80 and, more preferably, in a range between 1:0.01 and 0.8. As an example, the relationship between the molar ratio of L-ascorbic acid ($H_2$ Asc) to the iron (II) compound in the composition according to this invention to the deodorizing effect ($NH_3$ adsorption amount) is shown in FIG. 1.

In order to develop the activities of the composition according to this invention, it is required that the iron (II) compound, ascorbic acid or citric acid and alum are combined. This can be attained by dissolving each of the ingredients in a predetermined ratio into water to prepare an aqueous solution. Alternatively, the aqueous solution may be prepared into a powder through usual spray drying, freeze drying or the like.

The alum in the iron (II) compound composition according to this invention has a flame retarding effect, and a stabilizing deodorizing effect as well. The amount of the alum, while varying depending on the uses and the forms of the composition according to this invention, is within a range up to 100% by weight based on the total amount of the iron (II) compound and, ascorbic acid or citric acid, with the range between 2 and 20% by weight being preferred. While there is no particular restriction for the alum, potassium alum, ammonium alum, sodium alum or the like is preferred, with burnt alum being particularly preferred.

Further, the deodorizing effect and flame proofing effect of the composition according to this invention can further be improved by preferably incorporating a predetermined amount of sodium chloride. The amount of sodium chloride preferably ranges from 0.5 to 15% by weight based on the total amount of the iron (II) compound and ascorbic acid or citric acid.

The composition according to this invention is provided as an aqueous solution or as a drying product thereof i.e., as powders, granules, etc.

The concentration of the divalent iron ions in the aqueous solution, in view of the unique chemical activities of the aqueous solution, is generally more than 0.15% by weight and, preferably, more than 0.3% by weight calculated as metal iron with upper limit thereof being defined by the solubility of the (II) compound.

Since the composition according to this invention comprises a system of iron (II) compound, ascorbic acid and/or citric acid and alum, the divalent iron ions are extremely stabilized while maintained at an activated state. Accordingly, no substantial precipitation is formed even when the aqueous solution is brought into contact with air for a long period of time. Further, since the divalent iron ions are stabilized, they can endure the processing treatment under a high temperatures such as during spray drying. The thus obtained dried powder or the like is stable under the oxidative condition, which shows substantially the same extent of deodorizing and like other activities with those of the aqueous solution. Further, the dried substance requires no carrier or the like and is highly concentrated comprising 100% effective ingredients. Accordingly, it can be used not only by being dissolved again into water, but also being kneaded and mixed directly with cosmetics, pharmaceuticals, flame-retardants or resins.

Accordingly, upon using the composition of this invention, any method can be selected such as impregnation on a support, coating, scattering, kneading and the like and can be used broadly for deodorization, flame retardation, freshness preservation and growth promotion.

Although the reason why the composition according to this invention exhibits the unique activities is not yet clear, it is supposed that the molecular oxygen is converted into a super-oxide ($O_2^-$) with a strong oxidative power under the action of the divalent iron ions in the coexistence of ascorbic acid or citric acid as shown by the following schemes and this is kept at a stable state:

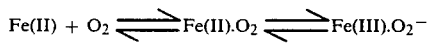

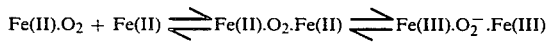

Further, it is considered that the bactericidal effect due to the super oxide also makes a contribution. While the mechanism of the flame-retarding effect is not clear at present, it is estimated that sodium chloride gives a specific effect.

The composition according to this invention will now be described more specifically for the respective effects.

(Deodorant)

The deodorant comprising the aqueous solution or the drying product thereof of the composition according to this invention can be applied for the purpose of eliminating offensive odors in toilets, garbage pails, refrigerators, drainage openings or the like, as well as for the removal of offensive odors in the space of the room interior. Referring to the application method of the deodorant, the aqueous solution may be used by spraying thereon or washing the source of the odor. In the case of a solid form, it may be applied directly to the source of offensive odor or, in addition, it may be placed in the area containing the offensive odor. The above mentioned deodorant may also be used by incorporating it in a sanitary material such as a diaper or a sanitary napkin.

As compared with the ordinary aqueous solution containing divalent iron ions, the aqueous solution of the composition according to this invention exhibits various unique chemical and physiological activities, which includes a significantly high deodorizing effect against offensive odor substances containing sulfur or nitrogen, for example, hydrogen sulfide, methylmercaptan, ammonia and trimethylamine. In order to form a solid deodorant, paper, synthetic paper, cloth, non-woven fabric, porous filler or like other solid materials may be impregnated with the aqueous solution, followed a drying treatment. If desirable, the drying treatment may be omitted. The porous fillers can include activated carbon, zeolite, bentonite, kaolin, pearlite, sepiolite, diatomaceous earth, silica, alumina and the like and can take any desired form such as a powder or granules. The total amount of L-ascorbic acid or citric acid, the iron (II) compound and alum carried on the solid substance is from about 0.5 to about 20 parts by weight as the solid component based on 100 parts by weight of the solid substance.

(Flame-retarding agent)

A Flame-retarding agent can be prepared by impregnating the aqueous solution of the composition according to this invention into burnable materials such as papers, fabrics (carpets, curtains, etc), fibers, yarns, woods, urethane resins and the like by means of coating, spraying and dipping. Further, the drying product may may be kneaded with a resin and formed, for example, into a film, or it may be spun after being mixed in a synthetic resin. The content of the retarding agent in the material to be treated, while different depending on the purpose of treatment the application of use of the material and the kind of the material, preferably ranges from 5 to 70 parts by weight based on 100 parts by weight of the material to be treated.

In this case, the material to be treated is given a flame retarding effect and a deodorizing effect together to form a multi-functional material.

(Freshness-preserving agent)

The third unique effect a composition according to this invention is the freshness-preserving effect and bactericidal activity. When the aqueous solution according to this invention is applied to fresh foods such as vegetables, fruits, meats, shellfish, and the like or their processed foods, these foods can be maintained a high degree of freshness over a prolonged period of time. In this case, the aqueous solution may be applied by coating or spraying it to the foods or by dipping the foods in the aqueous solution. Similar to the above-described case of the solid deodorant, the aqueous solution may also be impregnated onto a solid material such as papers, synthetic papers, woven fabrics, non-woven fabrics, yarns and porous fillers and then subjected to a drying treatment in order to form a solid freshness-preserving agent. Regarding the application method of such a solid freshness-preserving agent, in the case of a sheet- or film-like form, for example, the sheet or film may be used to wrap the foods. In a case of the powdery or granular form, said form may be admixed with other appropriate chemicals. Furthermore, the foods may be wrapped with a film of resin kneaded with the drying product of the composition according to this invention.

Furthermore, the freshness of the foods can also be preserved by placing them within a steam atmosphere of the aqueous solution of the composition according to this invention. In this case, the total concentration for the iron (II) compound, ascorbic acid or citric acid and alum as the effective ingredients in the aqueous composition, while different depending on the kind of the foods, amount of treatment, transferring velocity of the atmosphere and the like, lies within a range usually between from 0.1 to 40% by weight and, preferably, from 1.0 to 20% by weight. The humidity in this case is usually more than 80% and, preferably, more than 90%. Although there is no particular restriction for the temperature, excessively high temperature is undesirable and a temperature lower than the ambient temperature is preferred.

In addition, the steam atmosphere preferably circulated forcibly as necessary. It is particularly preferred to always replace a portion of the steam atmosphere with fresh steam so that the atmosphere containing the above-described effective ingredients are kept active. This can be attained specifically by releasing a portion of the atmosphere through at least one gap formed to a vinyl plastic house. However, the atmosphere is basically kept tightly closed.

The freshness-preserving agent is suitable to the application of freshness-preservation, antiseptic treatment and preservation for perishable foods such as vegetables, fruits, meats and shellfish or kneaded marine products. Specifically, this method can also be applied to a display case in a Sushi shop or a show case in a meat source or butchery. This method uses no harmful bactericides at all and comprises a combination of ingredients safe to men and animals. It can be practiced with no apprehension not only through the trading stage from producing districts to markets but also by end users such as house wives. It is particularly advantageous for attaining a consistent freshness-preserving system from the producing districts to the consumers. Further, the use of the freshness-preserving agent is advantageous in that no harmful damage is given to the human body at all to ensure safety even if the steam atmosphere leaks out of the system.

(Growth promoting agent for plants)

The unique physiological activity of the composition according to this invention resides in the effect of promoting plant growth. In this case, while there is no particular restriction in applying the composition according to this invention, there are methods, for instance, of placing plants in the steam atmosphere, as well as a method of watering the plants with the aqueous solution of the composition.

In using the composition of the plant growth promoting agent as an aqueous solution, the total concentration of the iron (II) compound, ascorbic acid or citric acid and alum as the effective ingredients in the solution, while different depending on the kind of the plants to be treated, amount of treatment and the transferring velocity of the atmosphere, usually ranges from 0.1 to 40% by weight, preferably, from 1.0 to 20% by weight.

For carrying out the growth promotion and the activating treatment for plants by the composition according to this invention, a steam atmosphere at high humidity is formed with the aqueous solution of the composition, for example, in which flowers and ornamental plants are placed. In this case, the humidity is usually more than 70% and, preferably, more than 90%. Further, although there is no particular restriction, excessively high or low temperatures are undesirable. The temperature ranges usually from 10° to 20° C. and, preferably, from 16° to 18° C.

In this case, although it is preferred to appropriately circulate the steam atmosphere forcibly it is particularly desirable to always replace a portion of the steam atmosphere with fresh steam so that the atmosphere containing the effective ingredients is maintained in an active state. This may be attained by forming the atmosphere within a vinyl plastic house or the like and forming gaps at least at a portion thereof. However, the atmosphere is basically kept tightly closed.

Although it is preferred that the treatment is carried out by forming the steam atmosphere within a transparent vinyl plastic film or the like as described above and under a sun light permeable condition, the purpose can sufficiently be obtained within a room.

The above-described method has a feature capable of promoting the growth of stalks and buds of the flowers and ornamental plants in a quick acting manner. Further, the method according to this invention has a meritous effect of improving the quality of the flowers and ornamental plants, since it can activate the potted plants to recover the dense green color and the luster of leaves, which have once become less vigorous being placed in a room or the like. Further, it is preferred to water paddy field rice plants or the like with the diluted aqueous solution according to this invention.

(Preparation of a plastic film)

A plastic film is prepared by incorporating a composition comprising the iron (II) compound, ascorbic acid and/or citric acid and alum into a resin.

The resin usable herein may either be a synthetic resin or natural resin. Specific examples can include polyolefins such as polyethylene and polypropylene, polyvinyl compounds such as polyvinyl alcohol, polyvinyl chloride, polyvinylidene chloride, polystyrene, and vinyl chloride-vinyl acetate copolymers, cellulose esters such as cellulose diacetate, regenerated cellulose, polyesters, polyamides, hydrochloride rubber, natural rubber and fluorine resins.

While varying depending on the application use and the material of the film, a preferred film thickness usually ranges from 0.01 to 0.5 mm but those films out of the above-mentioned range can also be prepared.

In the description of the present specification and claims, the term "film" does not mean to particularly restrict the thickness but it includes a so-called sheet-like material. Further, the term "plastic" does not mean thermoplasticity but means high molecular materials in the broader sense.

The content of the composition according to this invention in the film is preferably more than 0.5% by weight calculated as the solid component. A higher upper limit is better but the film becomes cloudy in excess of 5% by weight, imparting no particular problems for the fresh-preserving and deodorizing effects.

The plastic film can be prepared, in addition to the admixture of the composition according to this invention as a drying product, by ordinary film-forming processes for example, calendering method, T-die method, inflation method and solution casting method. Referring more specifically, in the case of the inflation method for instance, the iron (II) compound composition is preferably incorporated at first at a high concentration in the master pellet, which is further incorporated with a resin to dilute the concentration to about 1/10, followed by melt extrusion molding.

Further, it is also possible to add customary ingredients such as plasticizer, stabilizer, filler and other additives (such as pigment), within such a range so as not to impair the development of the activities of the composition according to this invention. If it is required to accelerate the devleopment of the activities of the composition according to this invention, from 3 to 10% by weight of sodium chloride may be mixed.

The thus obtained plastic film is a transparent film substantially equal in the appearance to that containing no iron (II) compound composition, although the smoothness is somewhat reduced. The use of the plastic film can provide an excellent effect capable of preserving the freshness of foods for a long period of time to prevent the perishment thereof. The film may preferably be applied for preserving the freshness, prevention of perishment and preservation of perishable fresh foods such as vegetables, fruits, meats and shellfish or kneaded marine products by packing and containing them therein. More specifically, it can be used as casing films for fish pastes (Kamaboko), sausages or the like. The material obtained according to this invention uses no harmful bactericides, at all and comprises a combination of ingredients safe to men and beasts. Further, the film also has a deodorizing effect to adsorb and remove the offensive and peculiar odors of foods.

(Preparation of functional wall paper)

A functional wall paper can be prepared by applying a coating of or incorporating the composition according to this invention to a wall paper material.

There is no particular restriction for the wall paper material usable in this invention and those conventionally employed so far can be used. While flame-retardant vinyl chloride resins are most preferred for the surface decorative layers, urethane resin, acrylic resin, polyethylene resin, polypropylene resin and polyester resin may also be used non-limitatively. Further, any of flame retardant papers, synthetic papers, inorganic papers and woven fabrics may be used as the substrate base cloth. In summary, the iron (II) composition can be applied to any wall paper material may be used.

Typical examples for the blend of the wall paper material made of vinyl chloride resin, which are most preferred, are shown.

| Blend (A) | Parts by weight |
|---|---|
| Vinyl chloride resin | 100 |
| Plasticizer (containing flame retardant plasticizer) | 60 |
| Foaming agent (ADCA) | 5 |
| Stabilizer | 3.5 |
| Filler | 10 |
| Flame retardant | 3 |
| Pigment | 30 |
| Total | 211.5 |

| Blend (B) | Parts by weight |
|---|---|
| Vinyl chloride resin | 100 |
| Plasticizer (containing flame retardant plasticizer) | 55 |
| Foaming agent (OBSH) | 2 |
| Stabilizer | 2 |
| Filler | 50 |
| Flame retardant | 3 |
| Pigment | 20 |
| Total | 232 |

Then, the iron (II) composition is applied by coating or incorporating it to the wall paper.

The coating may be applied by any method. Two preferred methods include (a) a method of utilizing a gravure printer and (b) a method of applying coating by a doctor knife i.e., spanishing. The steps are shown below.

(a) Method of utilizing a gravure printer

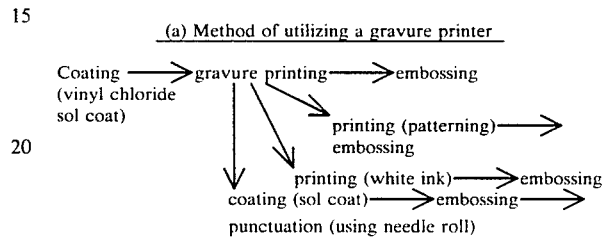

After gravure printing, the wall paper is dried at 120°–130° C. for 30–60 sec.

(b) Spanishing method by using a doctor knife

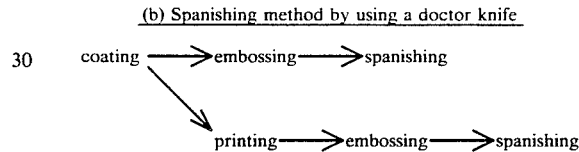

After spanishing, it is dried at 130°–140° C. for 1–1.5 min.

Upon such coating, an aqueous ink containing the composition according to this invention is used.

In the case of using the composition according to this invention as an aqueous solution, the concentration of the solid content is up to 30% by weight, at a maximum, in view of the relationship with the solubility. Since the aqueous ink may possibly be gelified if the solid content is too high, the amount should be less than 30% by weight and, preferably, 25% by weight and, in view of the fabrication stability, preferably from 15 to 20% by weight. As the basic composition for the aqueous ink, all known blendings of the gravure aqueous ink can be employed.

An example of the aqueous ink blended with the composition according to this invention is shown below.

| Ingredient | Parts by weight |
|---|---|
| VPA G medium | 90 |
| VPA G color | 10 |
| Aqueous solution of the composition according to this invention (solid content 20%) | 20 |
| Total | 120 |

(note)
VPA G medium: resin component (vinyl chloride-acrylic copolymer) 22%
VPA G color: resin component (ditto) 18–24% pigment content 3–15%

The coating amount of the aqueous ink in the gravure printing method (a) as described above, ranges usually from 10 to 40 g/m² and, preferably, from 20 to 30 g/m². In the above-described spanishing method (b) the coating amount ranges from 20 to 70 g/m² and, preferably, from 30 to 50 g/m².

In this case, if the coating amount is in excess of 70 g/m², it causes the problems of ink adhesion and the stability of the chromaticity at the surface. If the coating amount is insufficient no intended function can be obtained.

Next, the composition according to this invention may be used as powder. In this case, for instance, it may be blended, for example, in the paste sol of a vinyl chloride resin, into a paint composition, which is applied to the wall paper material with or without dilution to an appropriate concentration. One example of such painting composition is shown below.

| Ingredient | Parts by weight |
|---|---|
| Vinyl chloride paste resin | 100 |
| Plasticizer | 50 |
| Stabilizer | 2 |
| Composition according to this invention (ferrous fulfate: L-ascorbic acid = 1:0.03 (molar ratio), alum 10% by weight, particle size of several tens of micrometer) | 20 |
| Pigment | 20 |
| Total | 192 |

While it is required to apply a strong sharing force for dispersing the paint composition (for instance, by passing through paint rolls), the paint thus prepared can be used in the same manner as usual vinyl chloride paste sols.

The steps other than the coating step by the gravure printing or spanishing method, for instance the steps of printing and embossing, can be performed in the same manner as in the conventional preparation of wall papers.

Depending on the kinds of the wall paper material, the powder of the iron (II) composition may directly be kneaded into the wall paper material In this way, interior material provided with unique functions (air cleaning, deodorization, sterilization, and mold prevention) can be obtained.

The advantageous feature of the thus obtained wall paper resides not only in improving the aesthetic appearance of the room interior but also in cleaning the surrounding atmosphere and generating active oxygen which is extremely preferred biochemically. Although the deodorizing effect is one of the factors in this invention, this does not represent the entire effect but is a measure for each of the effects based on the active oxygen. Further, by applying punctuation to the wall paper, the air cleaning effect such as deodorization can be maintained for a long period of time.

Further, the wall paper has a flame proofing effect. Moreover, it maintains the activity capable of enduring heating such as emboss fabrication and foaming fabrication.

While the wall paper can be used in the same manner as the usual wall paper, it is particularly and preferably used for living rooms and toilets in ordinary houses, sick rooms and nurse stations in hospitals and the like.

BEST MODE FOR CARRYING OUT THE INVENTION

Figure 1:
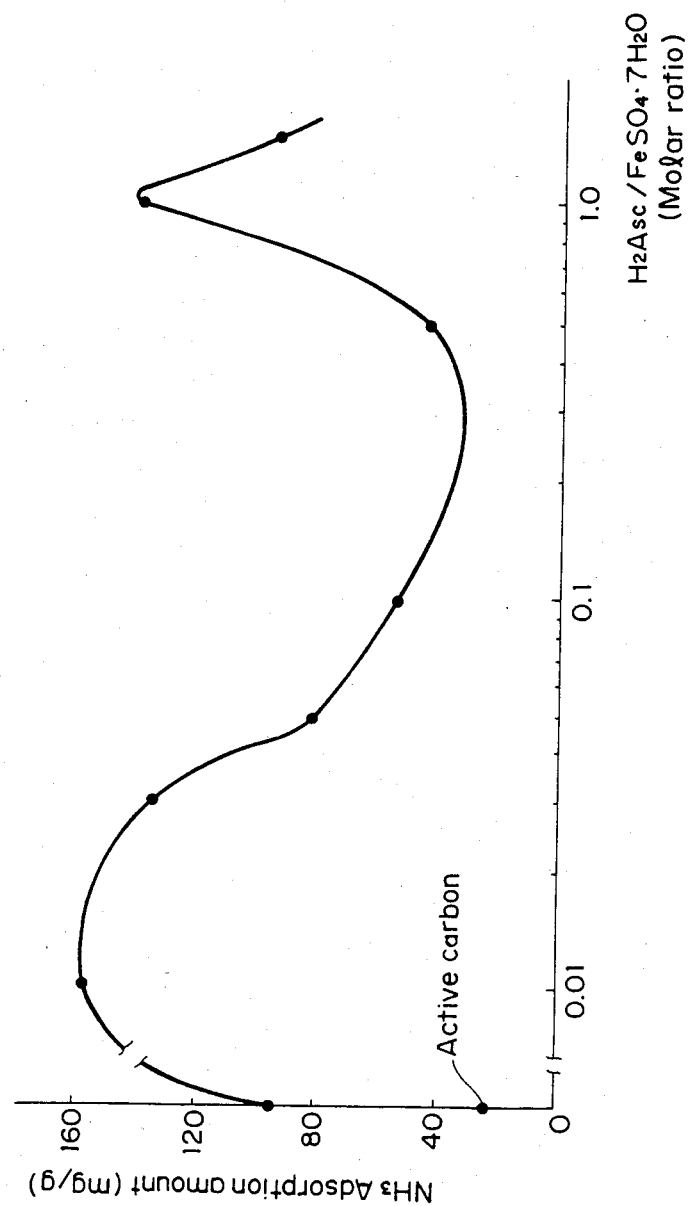
FIG. 1 is a graph showing a relationship between the molar ratio of L-ascorbic acid ($H_2$ Asc) to iron (II) compound in the composition according to this invention and the deodorizing effect ($NH_3$ adsorption amount)

This invention will next be described more specifically referring to examples.

EXAMPLE 1

(i) Preparation of Aqueous Solution (a) Solution A

After dissolving 27.5 g of ferrous sulfate heptahydrate (molecular weight 278.03) into water to 100 ml, 0.5 g of L-ascorbic acid were added and dissolved to prepare an undiluted solution, which was diluted to a twice volume with water.

(b) Solution B (composition according to this invention)

After adding 10 g of burnt alum to 100 ml of the undiluted solution (a) above and stirring for 30 min, the resultant solution was centrifugally separated and filtered. The thus obtained filtrate was diluted to a 2.5 times volume with water.

(c) Solution C

After adding 10 g of burnt alum to 100 ml of water and mixing for 30 min, the resultant solution was centrifugally separated and filtered. The thus obtained filtrate was used.

(d) Solution D 27.5 g of ferrous sulfate were completely dissolved into 100 ml of water, which was diluted to a twice volume with water.

(ii) Preparation of Treated Paper

The solutions A-D prepared as above were taken respectively to watch glass plates each with 9.3 cm diameter, in which Toyo Filter Papers Teisei No. 2 (9 cm diameter) were immersed for 30 min and then spontaneously dried over one night. In this way, treated papers A-D with the deposition amount about from 27 to 28 to 100 of the filter paper weight before treatment were obtained as shown in Table 1. The thus obtained treated papers, paper D turned yellow, while papers A, B turned pale brown and paper C remained white.

(iii) Flame-proofing Test

A flame of a flame height of 4 cm was prepared by using a gas burner in 1 cm inner diameter while not mixing air to a gas and the treated papers A-D each cut into a size of 1 cm width and 5 cm length were put into the flame from the top end of the flame for 2 cm length and the state when taken out from the flame was observed. The results are shown in Table-1.

TABLE 1

| Treated paper | Deposition amount (%) | The state of the residual flame and the degree of combustion after taking out from the flame |
|---|---|---|
| A | 27.5 | Burnt with flame. Kept to burn gradually after the extinguishment of the flame and completely consumed in about 25 sec, to leave reddish brown ash. |
| B | 28.5 | Resulted no flame. Gradually burnt and consumed in about 60 sec, to leave reddish brown ash. |
| C | 26.6 | Burnt with flame. Burnt for 7 sec after the extinguishment of the flame it carbonized. |

TABLE 1-continued

| Treated paper | Deposition amount (%) | The state of the residual flame and the degree of combustion after taking out from the flame |
|---|---|---|
| D | 26.3 | Burnt while entirely surrounded with the flame. Kept to burn for 20 sec after the extinguishment of the flame, to leave reddish brown ash. |

(note) The deposition amount is represented by % relative to the weight of the paper before treatment.

(iv) Deodorizing Test

Filter paper of 20 cm×29.5 cm (10 g weight) was treated by using 2.5 times dilution solution of the solution B (without the last 2.5 times dilution in the above-mentioned preparing method) to prepare treated papers in the same manner as described above. The deposition amount relative to the weight of the paper before treatment was about 50% by weight. The paper was cut into various sizes and placed in a vinyl plastic bag and tested for the deodorizing effect while adding 1 ml of aqueous ammonia (28% concentration). The results are shown in Table 2.

TABLE 2

| Size of the treated paper (cm) | Weight of the treated paper (cm) | Ammonia odor after 5 min | Ammonia odor after 40 min |
|---|---|---|---|
| 20 × 29.5 | 15 | none | none |
| 19 × 20 | 10 | none | none |
| 20 × 10.5 | 5 | slight | none |
| 10 × 14.5 | 4 | moderate | none |
| 9 × 10 | 3 | strong | none |

EXAMPLE 2

(i) Preparation of powdery composition of the iron (II) Compound

Ferrous sulfate (FeSO$_4$.7H$_2$O) and L-ascorbic acid (C$_6$H$_8$O$_6$) were mixed and dissolved in a 1:0.01 molar ratio to prepare an aqueous solution (the total concentration of the ferrous sulfate and ascorbic acid was about 28% by weight), to which 4% alum was dissolved. 500 g of the aqueous solution was spray-dried by using a spray drier (DL-21 manufactured by Yamato Kagaku K. K.) under the following conditions to combine the ferrous sulfate, and L-ascorbic acid to obtain a powdery composition containing alum (pH about 3.0).

| Operation condition | |
|---|---|
| Liquid feed rate | 40 ml/min |
| Spraying air flow rate | 15 l/min |
| Drying air flow rate | 6 m$^3$/min |
| Inlet temperature | 120° C. |
| Exit temperature | 75° C. |
| (Film formation by inflation method) | |

Then, 90 parts by weight of the master pellet of polypropylene and 10 parts by weight of the powdery composition of the iron (II) compound as described above were kneaded in a kneader at 200°–250° C. to form a premix. Further, 90 parts by weight of polypropylene were added to 10 parts by weight of the premix and kneaded at 220° C. form a film of 0.05 mm thickness by means of aeration (containing 1% by weight of iron (II) compound composition).

(ii) Freshness-preserving test

Respectively 10 pieces of lemon melon and peach bought from a market were divided into two groups. Each piece in one group was wrapped with a polypropylene film (cut from 24×30 cm into an appropriate size) containing the iron (II) compound composition and hermetically sealed through welding by electrical heat sealing.

Each piece in the other group was wrapped and hermetically sealed in the same manner with a commercially available plastic bag. Both groups were tightly closed in an ordinary manner with no evacuation. They were preserved at an ambient temperature (28° C.) and observed for freshness (chromaticity and luster on the epidermis, generation of mold, hardness of the pulp, the state of the bisected pulp, state of the calyx or the like). The results are shown in Table 3. As apparent from the results of the table, those wrapped with the film according to this invention can be preserved for about 2 weeks longer in the case of lemon and melon, and for about one week with perishable fruits such as peaches as compared with the use of conventional films.

(iii) Deodorizing Test

Figure 2:
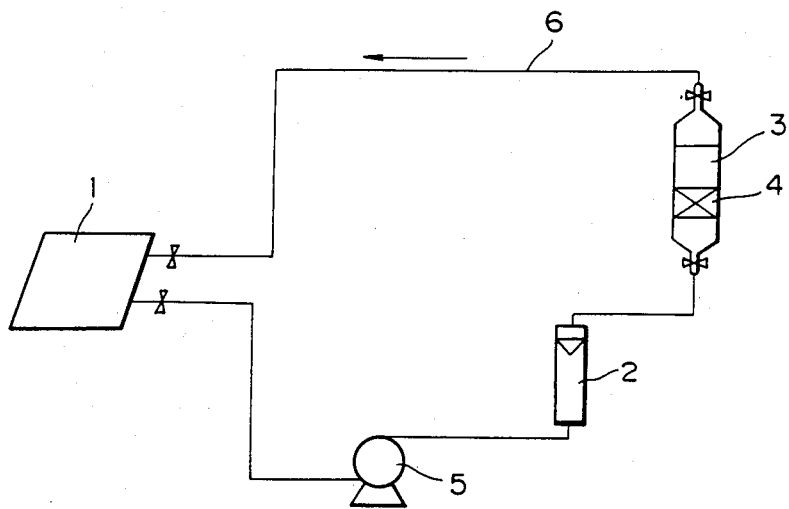
FIG. 2 is an explanatory view of an apparatus for deodorizing test.

The deodorizing test was carried out by using a test device assembled as shown in FIG. 2. In the figure, are shown a tetra-pack 1, a flowmeter 2, a column 3, and a pump 5. Five grams of polypropylene films according to this invention prepared in the same manner as above and finely cut into about 5 mm square were placed at 4 of the column. NH$_3$ gas was charged at 1700 ppm or 240 ppm concentration in the tetra-pack 1 and the entire system was connected. After circulating the gas for one hour, the concentration in the system was measured for the first time. The NH$_3$ gas was replaced with fresh gas at an identical concentration and the test was carried out in the same manner (the polypropylene specimens used were not replaced). In this way, the identical experiments were repeated for six times and the results are shown in Table 4 and Table 5.

TABLE 3

| | | 2nd day | 4th day | 7th day | 10th day | 13th day |
|---|---|---|---|---|---|---|
| Lemon | This invention | no change | no change | no change | no change | calyx recovered green the epidermis got luster |
| | Comparison invention | no change | epidermis lost luster | epidermis discolored, pulp softened | calyx blackened, luster lost and pulp softened further | pulp softened and shrinked entirely |

TABLE 3-continued

| | | | | | | |
|---|---|---|---|---|---|---|
| Melon | This invention | no change | no change | no change | no change | no change |
| | Comparative Example | no change | white mold occurred partially | white mold extended | white mold extended, pulp softened | white mold occurred entirely, pulp softened |
| Peach | This invention | no change | no change | no change | no change | no change |
| | Comparative Example | no change | no change | epidermis partially turned dark briwb | dark brown area extended | turned dark brown entirely, started to perish |

| | | 15th day | 17th day | 19th day | 20th day | 21th day |
|---|---|---|---|---|---|---|
| Lemon | This invention | calyx remained green with luster, and pulps was hard | calyx remained green with luster, and pulps was hard | calyx remained green with luster, and pulps was hard | calyx remained green with luster, and pulps was hard | pulps was sound and tasted sour |
| | Comparison invention | started to partially perish | perishment developed and deformation occurred | deformation occurred, slime released to completely putrify | — | — |
| Melon | This invention | no change | no change | no particular change, with luster | white mold occurred partially, but pulp remained hard | bisected pulp was sound |
| | Comparative Example | white mold occurred entirely, pulp softened | white mold occurred entirely, pulp softened | entirely covered with white mold, pulp softened | entirely covered with white mold, pulp softened | bisected pulp was diminished, entirely softened with putrid odor |
| Peach | This invention | epidermis lost tension slightly | epidermis partially turned dark grown | dark brown area of the epidermis extended | dark brown area of the epidermis extended pulp softened entirely | dark brown area of the epidermis further extended, pulp softened entirely |
| | Comparative Example | completely putridied, slime released | completely perished | — | — | — |

TABLE 4

| Ventilation (cycle) | 1 | 2 | 3 | 4 | 5 | 6 |
|---|---|---|---|---|---|---|
| Residual concentration (ppm) | 740 | 1200 | 1300 | 1400 | 1450 | 1500 |

(note)
Test condition
Offensive odor gas: NH$_3$
Gas concentration: 1700 ppm
Gas flow rate: 1 l/min
Ventilation time: 60 min
Column diameter: 24 mm φ
Bed height: 55 mm
Air temperature: 25° C.
Sample: pp sheet (kneaded with 1.0% iron (II) compound composition)
Sample weight: 5 g

TABLE 5

| Ventilation (cycle) | 1 | 2 | 3 | 4 | 5 | 6 |
|---|---|---|---|---|---|---|
| Residual concentration (ppm) | 100 | 140 | 160 | 170 | 180 | 190 |

(note)
Test condition
Offensive odor gas: NH$_3$
Gas concentration: 240 ppm
Gas flow rate: 1 l/min
Ventilation time: 60 min
Column diameter: 24 mm φ
Bed height: 55 mm
Air temperature: 27° C.
Sample: pp sheet (kneaded with 1.0% iron (II) compound composition)
Sample weight: 5 g

EXAMPLE 3

(Freshness-preserving agent)

27.5 g of ferrous sulfate heptahydrate (molecular weight 278.03) was dissolved with water to 100 ml. 0.5 g of L-ascorbic acid was then added and dissolved to prepare an undiluted aqueous solution of iron L-ascorbate.

Then, after dissolving 3% by weight of alum into the undiluted solution, said solution was then diluted twice with water to prepare an active aqueous solution.

An apparatus comprising a vinyl plastic house (91 cm width×54 cm depth×154 cm height) having a well ventilating medium shelf for placing foods and having a forcive humidifier ((ventilating amount, 1.2 liter/min) at the lower stage of the inside) (several mm of gaps are intesionally disposed to the joining portions for each of the sides) was assembled and the humidifier was operated after charging 20 liter of the freshness-reserving aqueous solution to the humidifier.

Banana (6 pieces in one bundle), raw shiitake (6 pieces), lemon (4 pieces), bought from the market were divided into two groups, in which one of the groups was placed on the shelf within the vinyl plastic house and the other was left in the room outside the vinyl plastic house. The aging change in the freshness for each of the foods was observed for 7 days with naked eyes. When the stationary state was attained after operating the humidifier, the temperature was 18° C. and the humidity was 90%. The room temperature was 19° C. and humidity was 70% outside the vinyl plastic house. The test results are shown in the Table 6 below.

It can be seen from the results of the Table below, that while the pulp softened and black bruises were increased on the bananas left at the room temperature for 7 days, the pulp did not soften but, rather, bruises in the epidermis were restored and disappeared on the bananas, utilizing the method of this invention. Accordingly, it can be seen that excellent freshness-preserving and quality-improving effects can be obtained by the method according to this invention. It is also apparent that the freshness can also be preserved for a long period of time in the case of raw shiitake and lemon by the method according to this invention. In the case of lemon, particularly, it is noted that the luster of the epidermis increased with the elapse of days.

TABLE 6

| Days of preservation | | Banana | Raw shiitake | Lemon |
|---|---|---|---|---|
| 1st day | This invention | no change | no change | no change |
| | Comparative example | no change | no change | no change |
| 2nd day | This invention | epidermis yellow rather intensive | no change | no change |
| | Comparative example | no change | no change | no change |
| 3rd day | This invention | Epidermis yellow further increased, black bruises decreased | no change | epidermis recovered luster |
| | Comparative example | black bruises on the epidermis increased a little | white area under the cap slightly turned brown | no change |
| 4th day | This invention | black bruises gradually decreased and epidermis recovered tension | no change | epidermis yellow became deep, luster increased further |
| | Comparative example | black bruises gradually extended | brown spots increased in the white area below the cap | luster lost and discolored |
| 5th day | This invention | black bruises almost disappeared, hardness increased | no change | luster increased further, the pulp hardened |
| | Comparative example | black bruises extended, pulp softened | brown spots in the white pulp increased, discoloration recognized | discolored, pulp softened |
| 6th day | This invention | black bruises entirely disappeared, hardness recovered | good luster at the dark brown area of epidermis calyx color showed no change | brilliant color, hard pulp |
| | Comparative Example | black bruises extended, softness increased | calyx brown color was deepened | discolored and softened further |
| 7th day | This invention | entirely appearance was fine, pulp was strong | good luster at the dark brown area of epidermis, no brown spots recognized in the white pulp | pulp had luster and strength and tasted much sour |
| | Comparative example | black bruises increased entirely, discolored and softened further | brown spots in the white area extended, white spots appeared in the dark brown surface epidermis | pulp lost luster, softened and tasted less sour |

EXAMPLE 4

(i) Growth promoting test for flowers and ornamental plants

An active aqueous solution was prepared in the same manner as in Example 3.

An apparatus comprising a vinyl plastic house casing (91 cm width×54 cm depth×154 cm height) having a well-ventilating medium shelf for placing plant pots and disposed with a forcive humidifier (ventilation amount 1.2 l/min) at the lower stage of the inside was assembled near the window within a room (disposed with slight (several mm) gaps at the joining portions for each of the sides), and the humidifier was operated after charging 20 liter of the active aqueous solution into the humidifier.

Respectively one pot of syunran (*cymbidium goeringii* rech f.), hanakilin (crown of thorns) and kinkouka (*narthecium asiaticum*) which had been bought were placed on the shelf within the vinyl plastic house. The other pots of syunran, hanakilin and kinkouka were left in the room outside the vinyl plastic house. The change in the growth of the plants were observed. When the stationary state was attained after operating the humidifier, the temperature was 18° C. and the humidity was 90%. The room temperature was 19° C. and humidity was 70% outside the vinyl plastic house. The test results are shown in Table 7.

TABLE 7

| Days of treatment | Item of the observation | Syunran (cymbidium goeringii rech f.) | | Harakilin (crown of thorns) | | Kirkouka (narthecium asiaticum) |
|---|---|---|---|---|---|---|
| | | extension of stalks and buds | color of leaves | extension of stalks and buds | color of leaves and stalks | color and luster of leaves |
| 1st day | This invention | no change | no change | no change | no change | no change |
| | Comparative example | no change | no change | no change | no change | no change |
| 2nd day | This invention | stalk developed 5 mm | no change | no change | brown stalk portion turned blueish | green deepened |
| | Comparative example | no change | no change | no change | no change | no change |
| 3rd day | This invention | stalks developed about 1 cm | green color deepened | buds emerged from the stalks, green leaves emerged | — | luster on the leave surface increased |
| | Comparative example | no change | no change | no change | no change | no change |
| 4th day | This invention | stalks developed about 1 cm, buds emerged | — | green leaves increased | stalk tip turned green | luster on the leave surface further increased |
| | Comparative example | no change | no change | no change | no change | no change |
| 5th day | This invention | stalk developed about 1 cm | green color further deepened | pale pink bud extended | — | leaf surface glistened, the rearface goe luster |
| | Comparative example | no change | no change | no change | no change | no change |
| 6th day | This invention | stalk developed about 1 cm | green color deepened, bloomed | pale pink bud extended | stalk turned green entirely from the tip | luster on both faces of leaves increased fruther |
| | Comparative example | no change | no change | no change | no change | no change |

(note)
1. Test was carried out at the end of February.
2. In the table "no change" means there was no remarkable changes.

(ii) Growing test for paddy field rice plant (Aqueous agent)

A solution prepared by dissolving 3% by weight of alum to the undiluted aqueous solution of iron L-ascorbate as prepared in Example 3 (hereinafter referred to as the aqueous agent according to this invention) was used.

The aqueous agent according to this invention, commercially available photosynthetic bacteria or ordinary water were applied to the soils of paddy field rice plants and the difference in the growing states was observed.

Step 1: Growing was observed for the group of seedlings grown to about 5 cm height in the nursery bed in the case of using water incorporated with the aqueous agent according to this invention and ordinary water (before transplantation)

Step 2: Change in the growth was observed to the paddy field (foamed styrol box) supplied with water containing the aqueous agent according to this invention, incorporated with photosynthetic bacteria and ordinary water after transplantation.

Step 3: The state of hull and rice were observed at the stage of ripening.

(Test Method)

1. Kind of soils used
Commercially available black soils and Arakida soil were mixed (2:1).
2. Observation for the growth in the nursery bed
Observation was made for the test lot divided into three lots.

(1) First lot: Grown only with tap water (referred to as tap water lot)
(2) Second lot: Grown with 100 times diluted aqueous solution according to this invention (100 times lot)
(3) Third lot: Grown with 400 times diluted aqueous solution according to this invention (400 times lot)
(4) Fourth lot: Grown with 1000 times diluted aqueous solution according to this invention (1000 times lot)
3. Observation for the growth after transplantation
After confirming the rooting of the seedlings at the elapse of five days from the transplantation, the composition of water in the paddy field was changed as below.
(1) Lot A: 100 cc of a solution prepared by adding 5% photosynthetic bacteria to 40 times the diluted aqueous solution according to this invention was applied to the paddy field of 400 times lot
(2) Lot B: 100 cc of 40 times the diluted solution of the aqueous agent according to this invention was applied to the paddy field of the 100 times lot.
(3) Lot C: 100 cc of 40 times the diluted solution of the aqueous agent according to this invention was applied to the paddy field of the 400 times lot.
(4) Lot D: Several drops of photosynthetic bacteria were added to the paddy field of the 1000 times lot.
(5) Lot E: Only tap water was added to the paddy field of the tap water lot.
(note) Adjustment of the water for the paddy field was carried out only for once and subsequent supply of water was conducted with tap water in any of the cases.

(Test Result)

1. Growing state in the nersury bed (after elapse of three weeks)

It took three weeks to reach the aimed seedling height of 10 cm, in which the seedlings in lot C (400 times lot) were higher than the seedlings in the other lots and they showed remarkable deep green color. There was no difference in other lots.

2. 16th day after the transplantation (1) The growth of seedling in the lots B and C was twice as compared with that in other lots, and the green color was deepened. The growth was satisfactory.

(2) The growing of the seedlings in lot A was next to the above and the height of the seedlings was about ⅔. They slightly turned yellow.

(3) In lots D and E, the height of the seedlings was about ½ to that in lots A, B. They exhibited some yellowing in the leaves. The growth was poor.

3. 27th day after the transplantation

The height of seedlings extended well, in which the growth in lots B, C was outstanding. Since there was a slight sign of yellowing at the outset, it was judged that the fertilizer was almost exhausted and a handful of a mixture of organic synthetic fertilizer and oil cake was applied to all of the lots.

4. 32th day after the transplantation

Green color was recovered from yellowing over all the lots. Particularly, the green color was deepened in lots B and C where remarkable growth was exhibited. The diameter of the stalks in the above lots was twice as large as in other lots.

5. 57th day after the transplantation

Earing was seen in the rice plants in lots A, B, C and E. No emergency of the ears was found only in lot D. Particularly, ears in lots B, C seemed sound and a number of hulls were counted in lots B, C.

6. 60th day after the transplantation

Ears were completely emerged in all of the lots.

7. 70th day after the transplantation

Ears began to sag in lots B, C. The hulls were solid. Ripening in the lot A was next to lots B and C. Hulls were empty in the lots D and E. The test results are shown in the table below.

TABLE 8

| Test lot | Number of hull | Size of grain | Length of stalk | Length of root |
|---|---|---|---|---|
| Lot A | 40–45 | small | 50–55 cm | 13 cm |
| Lot B, C | 55–60 | large | 65–70 cm | 17 cm |
| Lot D, E | 20–23 | none | 43–45 cm | 10 cm |

Summarizing the results of the test above, it was judged that the rice plants in lots B and C were grown as in the rich harvest type. The rice plants in lot A showed somewhat poor growth. The rice plants in lots D and E were grown quite in the bad harvest type. It was confirmed that a significant desirable effect was given for the growth of the paddy field rice plants by adding the aqueous agent according to this invention at the initial stage of the growing. In addition, a further development can be expected by applying a fertilizer to the soils upon transplantation.

EXAMPLE 5

An aqueous ink was prepared in the following composition, which was coated on an embossed wall paper made of vinyl chloride resin (the coating thickness of the vinyl chloride sol was between 160–200μ) by the spanishing method using a doctor knife.

| Aqueous ink | (parts by weight) |
|---|---|
| VPA G medium | 90 |
| VPA G color | 10 |
| Aqueous solution of iron (II) composition | 20 |
| Total | 120 |

The coating conditions are as below.

Coating amount: about 30 g/m$^2$

Treating rate: 15 m/min

Drying temperature: 120° C. for one min.

The aqueous solution of iron (II) composition was prepared by dissolving 27.5 g of ferrous sulfate heptahydrate (molecular weight 278.03) into water to 100 ml and adding and dissolving 0.5 g of L-ascorbic acid to prepare an undiluted solution and, thereafter, adding 10 g of burnt alum to 100 ml of the undiluted solution, stirring for 30 min and centrifugally separating them, followed by filtration.

The results of the test for the air cleaning effect on the thus treated wall paper is shown as tests (i)–(iii).

Test (i)

After placing filter paper (filter paper ¼ in 9 cm diameter) impregnated with chemicals such as formalin, artificial sweat and ammonia at the concentration as described below each by about 0.45 g in a polyethylenemade bag of 25×30 cm and further placing wall paper of 10 cm$^2$ specimens treated as described above to the bottom of the bag, the intensity of the odor in the bag was tested. The results are shown in Table 9 as Test No. 1. The test was further carried out for the case where the wall paper specimens were further heated at 180° C. for 20 sec (corresponding to emboss fabrication condition) or at 230° C. for one min (corresponding to forming fabrication condition) and the results are also shown in Table 9 as the Test No. 2 and No. 3. Concentration of Chemicals (1) Formalin: aqueous 5% solution (2) Artificial sweat solution: prepared according to JIS K 6772

(3) Ammonia: aqueous 1.25% solution (4) Cresol: aqueous 1% solution (5) hydrogen sulfide: an aqueous solution prepared by passing gaseous hydrogen sulfide for 5 min.

TABLE 9

| Test No. | | 1 | 2 | 3 |
|---|---|---|---|---|
| Heating | | — | 180° C. × 20 sec | 230° C. × 1 min |
| Formalin | 1 min | 3.8 | 3.7 | 4.0 |
| | 5 min | 3.1 | 3.6 | 3.6 |
| Artificial sweat solution | 1 min | 2.4 | 2 | 2.2 |
| | 5 min | 1.1 | 1.3 | 2.5 |
| Ammonia | 1 min | 2.8 | 2.3 | 3.2 |
| | 5 min | 1.6 | 1.4 | 2.3 |
| Hydrogen sulfide | 1 min | 2.5 | 2.0 | 2.3 |
| | 5 min | 1.6 | 1.7 | 1.7 |
| Cresol | 1 min | 2 | 2.2 | 2.2 |
| | 5 min | 1.3 | 2.0 | 1.7 |

(note)
Evaluation standards
1 no odor
2 slight odor
3 considerable odor
4 original odor did not change Numerical values of the data represent the average value for 10 test panelers.

Test (ii)

Then, the test was carried out for the air cleaning effect of the wall papers when placed in usual atmosphere for a certain period of time. The test was carried out on the wall papers heated at 230° C. for one min. The test results are shown in Table 10.

TABLE 10

| Chemicals | | 59.5.10 n = 5 | 59.5.18 n = 3 | 59.5.29 n = 4 | 59.6.7 n = 4 | 59.7.11 n = 4 |
|---|---|---|---|---|---|---|
| | | Date of measurement | | | | |
| Ammonia | 1 min | 2.8 | 2 | 3.6 | 2.5 | 2.5 |
| | 5 min | 1.6 | 1.5 | 2.8 | 1.7 | 1.8 |
| Cresol | 1 min | 2 | 2.5 | 2.9 | 3.4 | 3.0 |
| | 5 min | 1.3 | 1.8 | 2.0 | 2.9 | 2.0 |
| Artificial sweat solution | 1 min | 2.4 | 2.3 | 2.3 | 2.6 | 2.5 |
| | 5 min | 1.1 | 1.5 | 2.1 | 1.9 | 1.9 |
| Formalin | 1 min | 3.8 | 2.7 | 3.9 | | |
| | 5 min | 3.1 | 2.5 | 3.9 | | |

(note) The evaluation standards are the same as those in Table 9.

It is estimated from the results of the foregoing functional test that the wall papers according to this invention exhibit a deodorizing effect against offensive odor substances (except for formalin) generated in daily life, that the effect does not exhibit loss due to heating (about 230°0 C. × one min) at all and that the effect undergoes no remarkable effect due to aging change but rather loses stability for a considerable period of time.

Since the atmospheric concentration used in the foregoing test is at such a high level and not usually experienced in daily life while the effect is maintained under these conditions, it means that the wall papers can endure a long period of use.

Test (iii)

A deodorizing test was carried out by using a test apparatus assembled as shown in FIG. 2 in the same manner as in the deodorizing test (iii) in Example 2. Five grams of wall paper specimens finely cut into about 5 mm squares were placed in C and $NH_3$ gas at 5000 ppm concentration was charged (in A in the drawing) and the entire system was connected. After circulating the gas for one hour, the concentration was measured. A fresh gas ($NH_3$ concentration at 5000 ppm) was then charged in A (the wall paper specimens were placed as they were although the $NH_3$ gas was changed). Similar experiments were repeated for four times. The results of the experiment are shown in Table 11.

TABLE 11

| Ventilation (cycle) | 1 | 2 | 3 | 4 |
|---|---|---|---|---|
| Residual concentration (ppm) | 1050 | 4000 | 4500 | 4800 |

(note)
Test Condition
Offensive odor gas $NH_3$
Gas concentration 5,000 ppm
Gas flow rate 1 l/min
Ventilation time 80 min
Air temperature 27° C.
column diameter 24 mm φ
Bed height 68 mm
Sample wall paper
Sample weight 5 g

EXAMPLE 6

Paint was prepared by incorporating the powdery iron (II) composition in a vinyl chloride paste sol in the following composition.

| Ingredient | Parts by weight |
|---|---|
| Vinyl chloride paste resin | 100 |
| Plasticizer | 50 |
| Stabilizer | 2 |
| Powdery iron (II) composition (grain size of several tens μ order, ferrous sulfate: L-ascorbic acid = 1:0.03 (molar ratio)) | 20 |
| Pigment | 20 |
| Total | 192 |

By using the paint, wall papers were prepared as below. The coating thickness was 200μ.

Paint (iron (II) composition) ⟶ paint roll passage ⟶ coating ⟶ patterning treatment ⟶ embossing ⟶
(180-200° C., 5-10 sec)

punctuation (needle roll)

Punctuating fabrication to the surface of vinyl chloride is an essential condition for the wall papers prepared by mixing the powdery iron (II) composition into the vinyl chloride paste sol. The cleaning function of the wall paper specimens were then tested in the same manner as in Example 5. The results are shown in Table 12 Although the specimens are inferior in the quick acting effect than that of the wall papers obtained by the gravure coating method and the recess filling method, an extremely long lasting effect can be expected.

TABLE 12

| Chemical | Test sample | Wall paper kneaded with iron (II) composition |
|---|---|---|
| Ammonia | 1 min | 3.5 |
| | 5 min | 2.8 |
| Cresol | 1 min | 3.5 |
| | 5 min | 2.5 |

(note) The evaluation standards are the same as those in Table 9.

EXAMPLE 7

(Preparation of Aqueous composition)

The aqueous solution of the following composition was prepared.

TABLE 13

| Composition (parts by weight) | This invention | | | Comparative Example |
|---|---|---|---|---|
| | Experiment No. | | | |
| | 1 | 2 | 3 | 4 |
| Ferrous sulfate heptahydrate | 25 | 25 | 25 | 25 |
| Burnt alum | 3 | 3 | 3 | 3 |
| Citric acid | 3 | — | 3 | 3 |
| L-ascorbic acid | — | 0.5 | 0.5 | — |
| Sodium chloride | 3 | 3 | 3 | — |
| Dithionite | 0.3 | 0.3 | 0.3 | 0.3 |
| Water | balance | balance | balance | balance |
| Total | 100 | 100 | 100 | 100 |

When water draining garbage bags made of white Japanese paper were immersed in this solution and then dried spontaneously, they were colored a pale yellow with no unevenness in the solution of experiment Nos. 1-3 (solid deposition amount 15% by weight). They were stable after the elapse of one month. On the other hand, the bags immersed with the aqueous solution of experiment No. 4 was scarcely colored with only extremely pale color after drying, but it exhibited the color of brown iron rust after the elapse of one month to the loss of commercial value.

(Deodorizing Test)

Toyo Filter Paper Teisei No. 2 was immersed in the aqueous solutions of the experiment Nos. 1-3 and 4 and then spontaneously dried, to prepare treated papers 1-4 with a solid deposition amount of 20 based on 100 of the initial filter paper weights respectively.

The deodorizing test was carried out by using a test device assembled as shown in FIG. 2 in the same manner as the deodorizing test (iii) in Example 2. Five grams of the treated paper 1 or 4 prepared as above and finely divided into about 5 mm squares were placed in C, $NH_3$ gas at 1700 ppm or 18000 ppm concentration was charged into A and the entire system was connected. After recycling the gas for one hour, the concentration was measured for the first. The same test was carried out while replacing the gas with the fresh $NH_3$ gas at the same concentration (the treated paper specimens were left unchanged). In this way, the identical experiment was repeated for 8 times. The results are shown in Table 14 and Table 15.

TABLE 14

| Ventilation (cycle) | 1 | 2 | 3 | 4 | 5 | 6 | 7 | 8 |
|---|---|---|---|---|---|---|---|---|
| Residual concentration (ppm) | 0.4 | 0.5 | 0.8 | 5.5 | 15 | 40 | 160 | 3800 |

(note)
Measuring Condition
Offensive odor gas       $NH_3$
Gas concentration        18000 ppm
Gas flow rate            1 l/min
Ventilation time         60 min
Air temperature          26° C.
column diameter          24 mm φ
Bed height               52 mm
Sample                   treated paper 1
Sample weight            5 g

TABLE 15

| Ventilation (cycle) | 1 | 2 | 3 | 4 | 5 | 6 | 7 | 8 |
|---|---|---|---|---|---|---|---|---|
| Residual concentration (ppm) | 1.0 | 1.0 | 3.5 | 2.0 | 5.0 | 30 | 330 | 7500 |

(note)
Measuring Condition
Offensive odor gas       $NH_3$
Gas concentration        17000 ppm
Gas flow rate            1 l/min
Ventilation time         60 min
Air temperature          27° C.
column diameter          24 mm φ
Bed height               75 mm
Sample                   treated paper 4
Sample weight            5 g (Flame-proofing test)

A flame of 4 cm length was prepared by a gas burner of 1 cm inner diameter while not mixing air with gas. Treated papers 1-3 were then put into the flame in two sec from the top end of the flame for 2 cm lengths, they neither produced flames nor burnt, with the carbonized products remaining.

A formed urethane sheet was impregnating with the aqueous compositions of experiment Nos. 1-3 and 4 as described above to prepare treated urethane materials with 20% by weight of the solid content. They were subjected to a flame proofing test in the same manner as described above. Although experiment No. 4 burnt with flame, experiment Nos. 1-3 neither produced flame nor burnt, with carbonized products remaining.

We claim:

1. A chemically active composition containing divalent iron ions, which comprises an iron (II) compound; ascorbic acid and/or citric acid; and alum, wherein the ratio between the divalent iron ions in the iron (II) compound and ascorbic acid or citric acid is between 1:0.02 and 0.30 (in the case of ascorbic acid) or 1:0.01 and 0.80 (in the case of citric acid) by weight ratio; and wherein the alum is present in an amount of from 2 to 100% by weight based on the total amount of the iron (II) compound, ascorbic acid and/or citric acid.

2. The composition as claimed in claim 1, which comprises citric acid.

3. The composition as defined in claim 1, which is an aqueous solution.

4. The composition as defined in claim 1, which is a drying product of the aqueous solution.

5. The composition as defined in claim 1, which contains sodium chloride.

6. A deodorant, freshness-preserving agent for foods, growth promoting agent for plants and flame-retardant for burnable materials comprising the composition as defined in claim 1.

7. A multi-functional material prepared by incorporating the composition as defined in claim 1 by way of impregnation, coating, dipping, spraying or, kneading.

8. A food preservative chemically active composition containing divalent iron ions, comprising an iron (II) compound; ascorbic acid and/or citric acid; and alum wherein the ratio between the divalent iron ions in the iron (II) compound and ascorbic acid or citric acid is between 1:0.02 and 0.30 (in the case of ascorbic acid) or 1:0.01 and 0.80 (in the case of citric acid) by weight ratio: and wherein the alum is present in an amount of from 2 to 100% by weight based on the total amount of the iron (II) compound, ascorbic acid and/or citric acid.

9. The composition as claimed in claim 1, wherein the ratio between the divalent iron ions in the iron (II) compound and ascorbic acid is in the range of 1:02 1:0.13.

10. The composition as claimed in claim 1, wherein the amount of alum is from 2 to 20% by weight based on the total amount of the iron (II) compound, ascorbic acid and/or citric acid.

11. The composition as claimed in claim 1, which comprises ascorbic acid.

12. The composition as claimed in claim 1, which comprises ascorbic acid in combination with citric acid.

13. A method of food preservation by applying to said foods a food preservative effective amount of the composition of claim 1.

14. A method of promoting the growth of plants by adding to said plants a growth promoting effective amount of the composition of claim 1.

15. A method of flame retardation by adding to a burnable material a flame retarding effective amount of the composition of claim 1.

16. A method of deodorizing by adding to offensive odors a deodorizing effective amount of the composition of claim 1.

17. A method of food preservation by applying to said foods a food preservative effective amount of the composition of claim 8.

18. A method of promoting the growth of plants by adding to said plants a growth promoting effective amount of the composition of claim 8.

19. A method of flame retardation by adding to a burnable material a flame retarding effective amount of the composition of claim 8.

20. A method of deodorizing by adding to offensive odors a deodorizing effective amount of the composition of claim 8.

* * * * *